(12) United States Patent
Mishima et al.

(10) Patent No.: US 6,641,570 B2
(45) Date of Patent: Nov. 4, 2003

(54) DISPOSABLE DIAPER

(75) Inventors: Yoshitaka Mishima, Kagawa-ken (JP); Koichiro Tani, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 09/901,385

(22) Filed: Jul. 9, 2001

(65) Prior Publication Data

US 2002/0010453 A1 Jan. 24, 2002

(30) Foreign Application Priority Data

Jul. 21, 2000 (JP) ........................................ 2000-221037

(51) Int. Cl.[7] ................................................ A61F 13/15
(52) U.S. Cl. ........................... 604/385.28; 604/385.27; 604/385.01; 604/385.24; 604/385.26
(58) Field of Search ..................... 604/385.01, 385.101, 604/385.28, 385.24, 385.25, 385.26, 385.27

(56) References Cited

U.S. PATENT DOCUMENTS

| 719,811 | A | * | 2/1903 | Kent | |
|---|---|---|---|---|---|
| 810,689 | A | * | 1/1906 | Way | |
| 3,626,943 | A | * | 12/1971 | Worcester | 128/286 |
| 5,649,918 | A | | 7/1997 | Schleinz | |
| 5,792,130 | A | * | 8/1998 | Widlund et al. | 604/385.1 |
| 6,017,336 | A | | 1/2000 | Sauer | |
| 6,402,729 | B1 | * | 6/2002 | Boberg et al. | 604/385.28 |
| 6,409,711 | B1 | * | 6/2002 | Jonbrink | 604/385.01 |

FOREIGN PATENT DOCUMENTS

| EP | 0 908 162 A2 | 4/1999 |
|---|---|---|
| JP | 11-113958 | 4/1999 |
| WO | WO 95/25493 | 9/1995 |
| WO | WO 97/14385 | 4/1997 |
| WO | WO 98/08476 | 3/1998 |

OTHER PUBLICATIONS

European search report mailed Feb. 1, 2002.

* cited by examiner

Primary Examiner—Weilun Lo
Assistant Examiner—Jacqueline F Stephens
(74) Attorney, Agent, or Firm—Butzel Long

(57) ABSTRACT

A disposable diaper that includes a panel structure composed of a base sheet and a core attached thereto and a sheet member 9 extending above the panel structure. The panel structure has a pair of first side slaps extending in a longitudinal direction and a pair of end flaps extending in a transverse direction. The sheet member includes a pair of side walls biased to rise above the panel structure and a top wall biased to be spaced upward from the panel structure. The side walls have side edge portions bonded to the vicinity of transversely opposite side edges of the core and first end portions bonded to the end flaps. The top wall has an opening defined between the side walls, second end portions bonded to the end flaps and second side flaps extending outside the top edges of the respective side walls 10 in parallel to the first side flaps. Transversely opposite side edge portion of these flaps that overlap each other in the front and rear waist regions are bonded to each other.

4 Claims, 6 Drawing Sheets

DISPOSABLE DIAPER

BACKGROUND OF THE INVENTION

This invention relates to a disposable diaper adapted to absorb and to hold excretion discharged thereon.

Japanese Patent Application Publication No. 1999-113958A describes a disposable diaper basically comprising a panel structure which comprises, in turn, a liquid-pervious topsheet, a liquid-impervious backsheet and a liquid-absorbent core disposed between these two sheets, and a sheet member lying above the topsheet. The panel structure is longitudinally composed of a front waist region, a rear waist region and a crotch region extending between these waist regions wherein a pair of side flaps extend in a longitudinal direction immediately outside transversely opposite side edges of the core and a pair of end flaps extend in a transverse direction immediately outside longitudinally opposite ends of the core. The sheet member comprises a pair of side walls extending in the longitudinal direction in the vicinity of the transversely opposite side edges of the core and a top wall extending between top edges of the respective side walls in parallel to the top- and backsheets.

The respective side walls have the side edge portions thereof bonded to the vicinity of the side edges of the core in the panel structure and the longitudinal opposite ends thereof bonded to the end flaps of the panel structure. The top wall has an opening at a location corresponding to a middle zone of the crotch region and longitudinally opposite end portions bonded to the end flaps. This diaper of prior art enables the respective side walls to rise above the panel structure and enables the top wall to be spaced upward from the panel structure so that a cavity adapted to receive excretion discharged on the diaper may be defined between the panel structure and the sheet member as the top wall is spaced upward from the panel structure.

The top wall of the sheet member is of a rectangular shape transversely dimensioned to be smaller than a transverse dimension of the panel structure and not present above the side flaps of the panel structure. The side walls of the sheet member are bonded to the panel structure except its end flaps only along the side edge portions of the side walls. As a result, the sheet member is not restricted by the panel structure and freely movable.

In the case of the diaper disclosed by above-identified Publication, the top wall comes in contact with wearer's belly and hip merely over a small area in the front and rear waist regions of the diaper as the diaper is put on the wearer's body and the sheet member is movable independently of the panel structure. Consequently, the sheet member often shifts particularly in the transverse direction in the front and rear waist regions. Such transverse shift of the sheet member may lead to a problem that the opening formed in the top wall may miss the extent of the wearer's urinary organs and/or anus and be unable to receive excretion into the cavity.

SUMMARY OF THE INVENTION

It is an object of this invention to provide a disposable diaper improved so that the top wall of the sheet member may come in close contact with a wearer's belly and hip over a relatively large area and the sheet member may be sufficiently prevented from shifting sideways in the front and rear waist regions to receive excretion reliably into the cavity.

According to this invention, there is provided a disposable diaper comprising: a panel structure including a liquid-impervious base sheet and a liquid-absorbent core attached thereto and a sheet member extending above the panel structure; the panel structure having a front waist region, a rear waist region and a crotch region extending between these waist regions and including a pair of first side flaps extending in the longitudinal direction immediately outside transversely opposite side edges of the core and a pair of end flaps extending in a transverse direction immediately outside longitudinally opposite ends of the core; the sheet member including a pair of side walls extending in the longitudinal direction in the vicinity of the transversely opposite side edges of the core so that the side walls are normally biased to rise above the panel structure and a top wall extending between top edges of the side walls in parallel to the base sheet so that the top wall is normally biased to be spaced apart from upward from the panel structure; the side walls respectively comprising side edge portions bonded to the core in the vicinity of the transversely opposite side edges thereof and first end portions bonded to the end flaps; the top wall having at least one opening defined between the side walls and second end portions bonded to the end flaps so that a cavity adapted to receive excretion is defined between the panel structure and the sheet member.

According to this invention, the top wall has a pair of second side flaps extending immediately outside the top edges of the side walls in parallel to the first side flaps so that the first side flap and the second side flap are bonded together at least along the transversely opposite side edge portions of the first and second side flaps overlapping each other in the front and rear waist regions.

According to one embodiment of this invention, at least the top wall of the sheet member is elastically stretchable at least in the longitudinal direction of the longitudinal and transverse directions and bonded under tension in the longitudinal direction to the panel structure so that the side walls may be normally biased to rise above the base sheet and the top wall may be normally biased to be spaced apart from the base sheet.

According to another embodiment of this invention, the first and second side flaps have transversely opposite side edges thereof curving inward in the transverse direction in the crotch region so as to describe circular arcs so that the top wall has a transverse dimension in the crotch region smaller than the corresponding dimension in the panel structure.

DETAILED DESCRIPTION OF THE PREFERRED EMBODIMENTS

Details of a disposable diaper according to this invention will be more fully understood from the description given hereunder with reference to the accompanying drawings.

Figure 1:
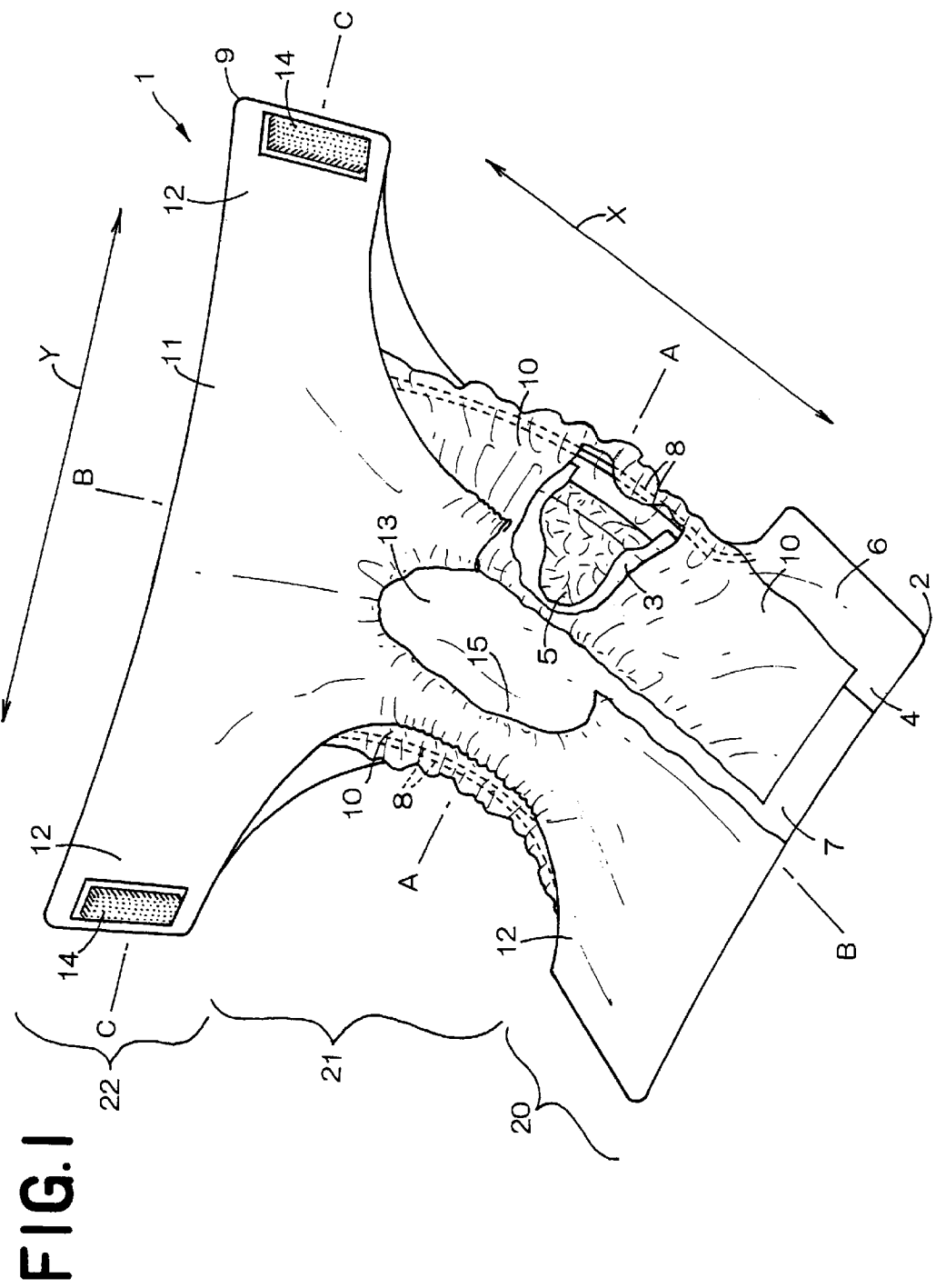
FIG. 1 is a perspective view showing a disposable diaper according to this invention as partially broken away.
Figure 2:
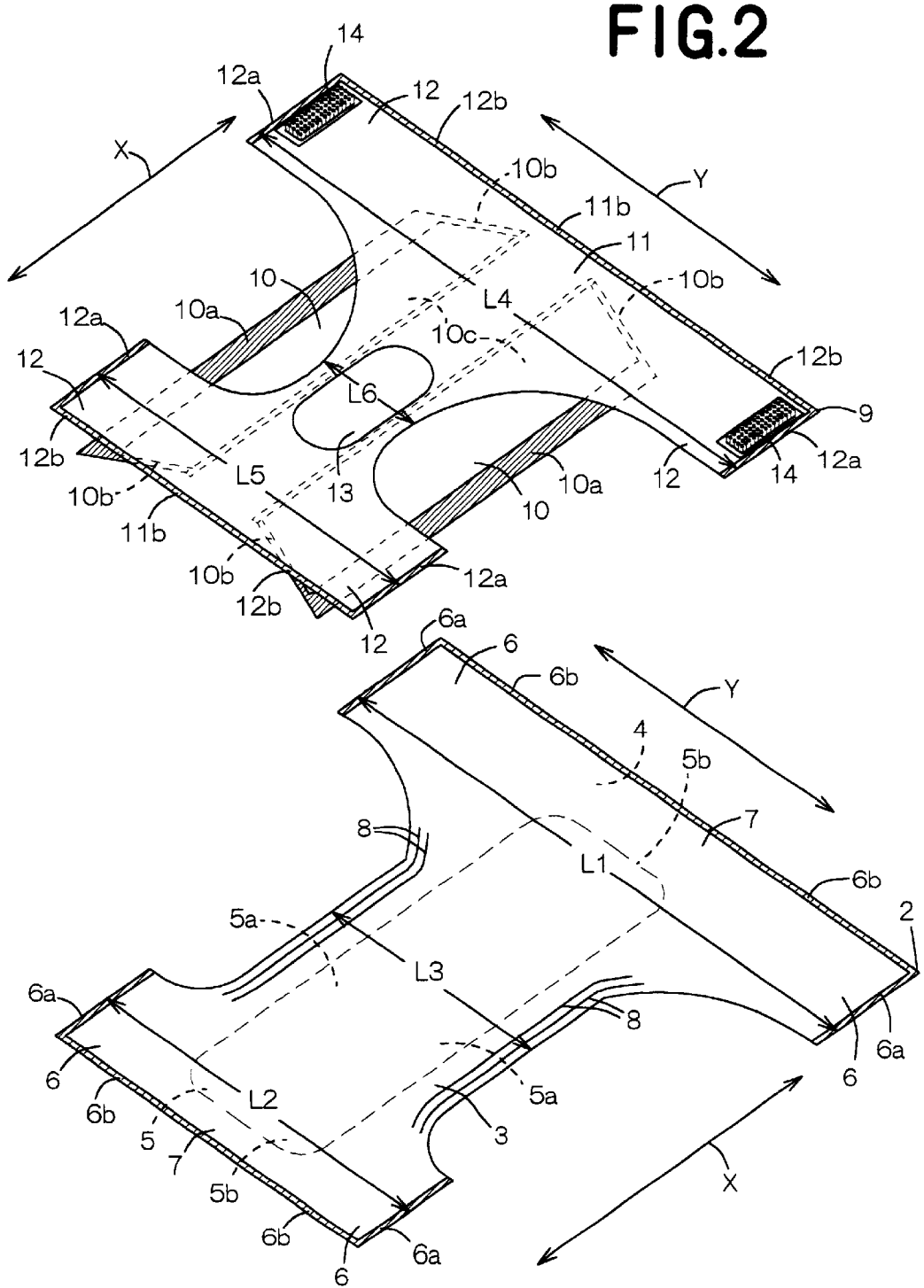
FIG. 2 is an exploded perspective view showing the diaper as a basic structure of the diaper and a liquid-resistant sheet member being separated from each other.

FIG. 1 is a perspective view showing a disposable diaper 1 according to this invention as partially broken away and FIG. 2 is an exploded perspective view showing the diaper 1 as a panel structure 2 and a sheet member 9 being separated from each other. It should be understood that, in the embodiment illustrated and described herein, a longitudinal direction is designated by X and a transverse direction is designated by Y as indicated by arrows X and Y, respectively, in FIGS. 1 and 2.

The diaper 1 basically comprises a panel structure 2 and a sheet member 9 extending above the panel structure 2. The panel structure 2 basically comprises, in turn, a liquid-pervious topsheet 3, a liquid-impervious backsheet 4 and a liquid-absorbent core 5 disposed between these two sheets 3, 4 and entirely covered with and bonded to water-absorbent tissue paper (not shown). Both the top- and backsheets 3, 4 are elastically stretchable longitudinally as well as transversely. The core 5 is intermittently bonded to the inner surface of the top- and/or backsheets with tissue paper therebetween.

The topsheet 3 is not an essential component member for the panel structure 2. It is also possible to form the panel structure 2 from the liquid-impervious backsheet 4 and the liquid-absorbent core 5 attached to the inner surface of the backsheet 4 in the absence of the topsheet 3.

The panel structure 2 is longitudinally composed of a front waist region 20, a rear waist region 22 and a crotch region 21 extending between these front and rear waist regions 20, 22. The panel structure 2 further comprises a pair of side flaps 6 longitudinally extending in parallel to each other along transversely opposite side edges 5a of the core 5 and a pair of end flaps 7 transversely extending in parallel to each other immediately outside longitudinally opposite ends 5b of the core 5. In the panel structure 2, the first side flaps 6 curve transversely inward in the crotch region 21 so as to describe circular arcs and, in consequence, the panel structure 2 is hourglass-shaped as viewed in its plan view. The panel structure 2 has its transverse dimension L1 in the rear waist region 22 larger than its transverse dimension L2 in the front waist region 20.

The first side flaps 6 are formed from portions of the top- and backsheets 3, 4 extending transversely outward beyond the transversely opposite side edges 5a of the core 5. A longitudinally extending elastic member 8 is bonded under tension to each of the first side flaps 6. The end flaps 7 are formed from portions of the top- and backsheets 3, 4 extending longitudinally outward beyond longitudinally opposite ends 5b of the core 5. In the first side flaps 6 and the end flaps 7, said portions of the top- and backsheets 3, 4 placed upon each other are intermittently bonded without tension to each other.

The sheet member 9 is formed by a pair of side walls 10 longitudinally extending in the vicinity of the transversely opposite side edges 5a of the core 5 and a top wall 11 extending above the respective side walls 10 in parallel to the top- and backsheets 3, 4. The sidewalls 10 and the top wall 11 are formed with separate sheets, respectively, and hereinafter the side walls 10 will be referred to as side wall sheets 10 and the top wall 11 will be referred to as the top wall sheet 11.

Each of the side wall sheets 10 comprises a first side edge portion 10a overlapping the associated first side flap 6, an end portion 10b overlapping the associated the end flap 7 and a top edge portion 10c extending longitudinally above the side edge portion 10a. The side wall sheet 10 is elastically stretchable longitudinally as well as transversely.

The top wall sheet 11 comprises second side flaps 12 lying outside the top edge portions 10c of the respective side wall sheets 10 and extending in parallel to the respective first side flaps 6, a longitudinally larger opening 13 defined between the top edge portions 10c of the respective side wall sheets 10 and second end portions 11b overlapping the respective end flaps 7. The top wall sheet 11 is elastically stretchable longitudinally as well as transversely. In the top wall sheet 11, the second side flaps 12 curve transversely inward to describe circular arcs and thereby define an hourglass-like configuration, as viewed in the plan view, in the crotch region 21.

The top wall sheet 11 has its transverse dimension L4 in the rear waist region 22 is larger than its transverse dimension L5 in the front waist region 20. Its transverse dimension L6 in the crotch region 21 is smaller than a transverse dimension L3 of the panel structure 2 in the crotch region 21.

The top wall sheet 11 is bonded to the top edge portions of the respective side wall sheets 10. The side wall sheets 10 and the top wall sheet 11 are not under any tension when these sheets 10, 11 are bonded together. A pair of rectangular hook members 14 are attached to transversely opposite second flaps 12, respectively, in the rear waist region 22.

Figure 3:
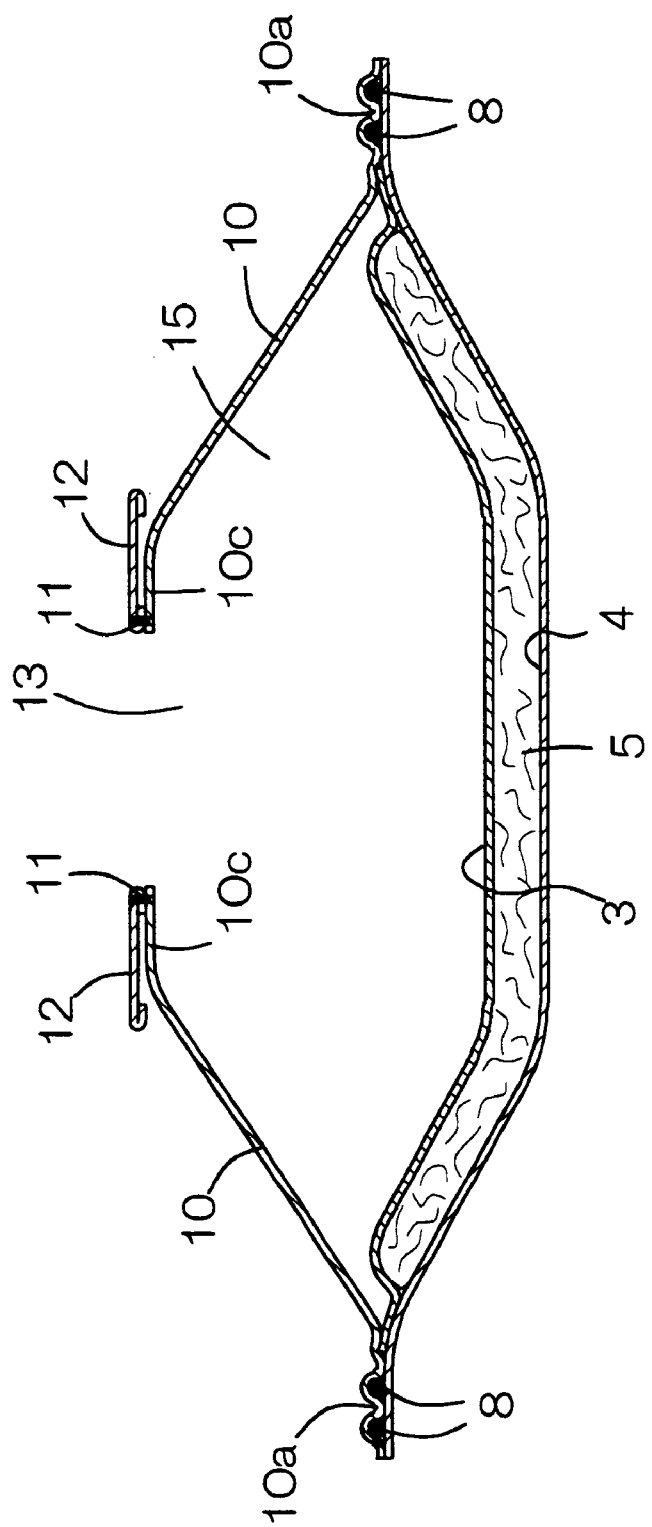
FIG. 3 is a sectional view taken along a line A—A in FIG. 1.
Figure 4:
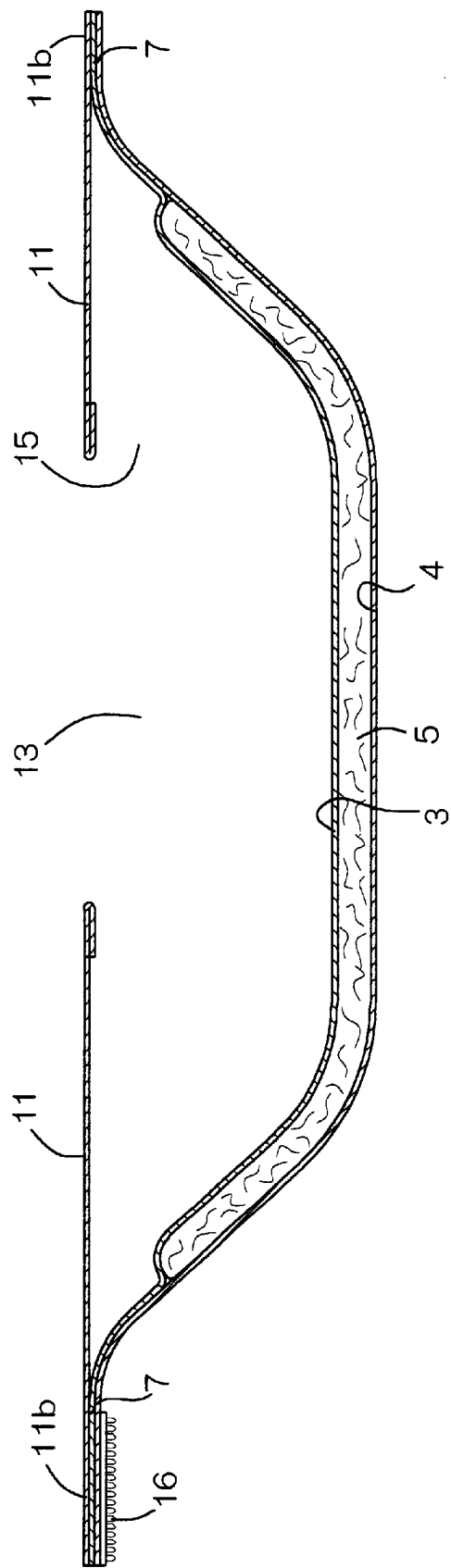
FIG. 4 is a sectional view taken along a line B—B in FIG. 1.
Figure 5:
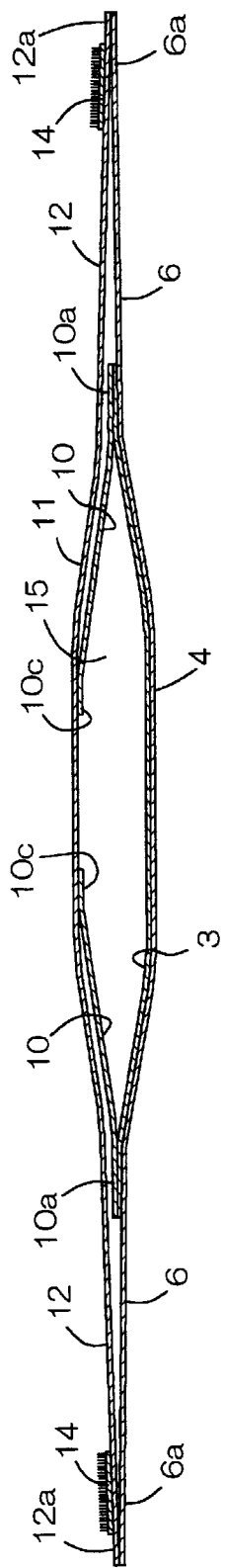
FIG. 5 is a sectional view taken along a line C—C in FIG. 1.

FIGS. 3, 4 and 5 are sectional views taken along lines A—A, B—B and C—C in FIG. 1, respectively.

In the first side flaps 6, the topsheet 3 extends transversely outward slightly beyond the transversely opposite side edges 5a of the core 5 and the backsheet 4 extends transversely outward beyond the side edges of the topsheet 3.

The side wall sheets 10 have the side edge portions 10a thereof bonded to the top- and backsheets 3, 4 of the panel structure 2 in the first side flaps 6 and the end portions 10b thereof bonded to the topsheet 3 of the panel structure 2 in the end flaps 7. The top wall sheet 11 has its end portions 11b bonded to the topsheet 3 of the panel structure 2 in the end flaps 7. The first side flaps 6 and the second side flaps 12 are bonded together along the transversely opposite side edge portions 6a, 12a of these flaps 6, 12 overlapping one another in the front and rear waist regions 20, 22 and the longitudinally ends 6b, 12b of these flaps 6, 12 overlapping one another in these flaps 6, 12.

When the side wall sheets 10 and the top wall sheet 11 are bonded to the panel structure 2, the top- and backsheets 3, 4 are free from any tension while the side wall sheets 10 and the top wall sheet 11 are under tension in their longitudinal direction.

In the diaper 1, the side wall sheets 10 and the top wall sheet 11 contract in the longitudinal direction so that the panel structure 2 longitudinally curves with the topsheet 3 inside. The side wall sheets 10 thus rise above the panel structure 2 and the top wall sheets 11 are spaced upward from the panel structure 2. In this manner, the topsheet 3, the side wall sheets 10 and the top wall sheet 11 surround a cavity 15.

Figure 6:
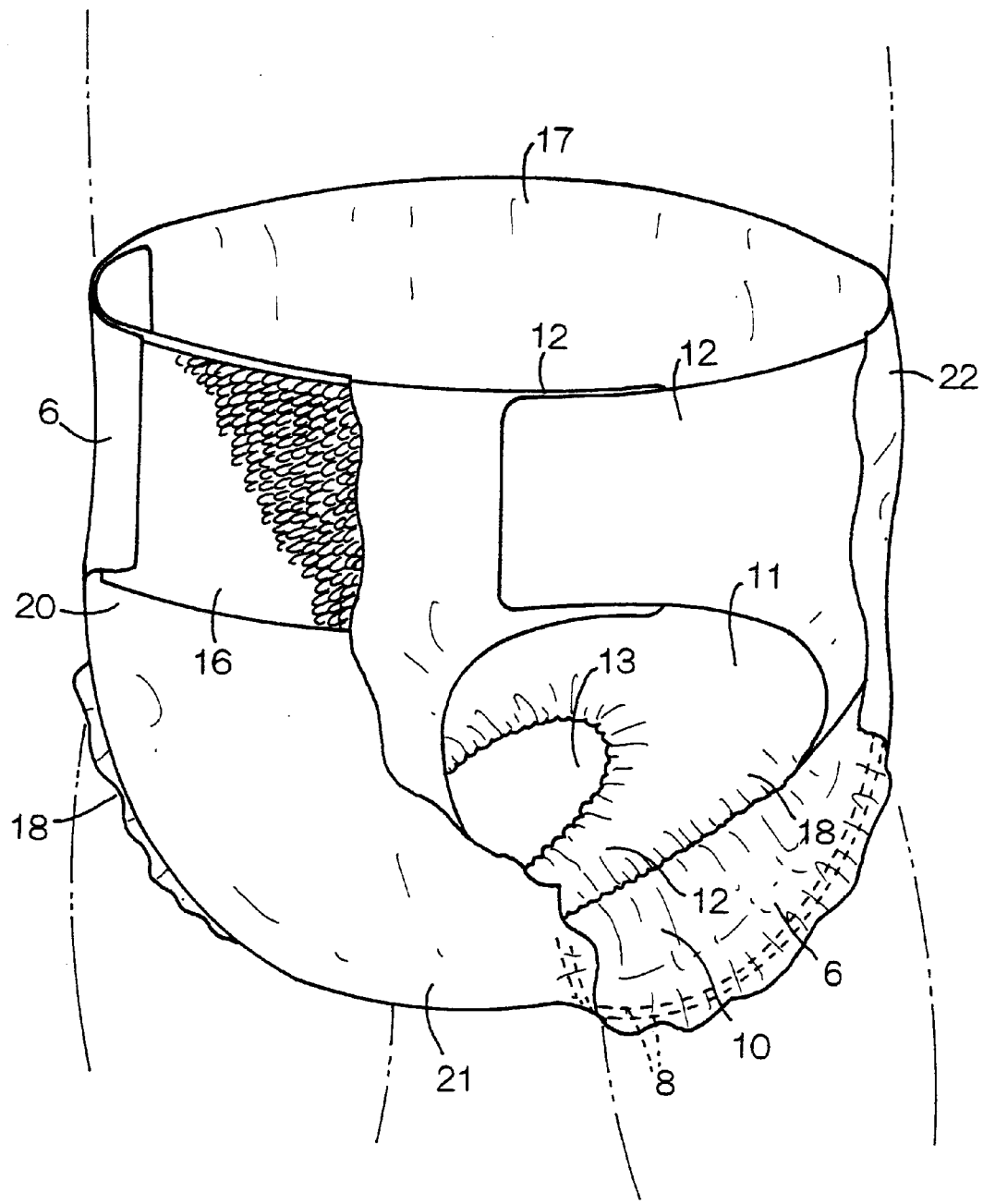
FIG. 6 is a perspective view showing the diaper as put on a wearer's body and as partially broken away.

FIG. 6 is a perspective view showing the diaper 1 as put on a wearer's body and as partially broken away, in which the wearer is indicated by chain lines. To put the diaper 1 on the wearer's body, the second side flaps 12 in the rear waist region 22 are overlapped upon the first side flaps 6 in the front waist region 20, and then and the hook members 14 are anchored on associated loop members 16 attached to the front waist region 20 of the panel structure 2 to connect the front and rear waist regions 20, 22 to each other. Referring to FIG. 6, the diaper 1 is formed with a waist-hole 17 and a pair of leg-holes 18. Excretion is received by the cavity 15 through the opening 13.

The side wall sheets 10 and the top wall sheet 11 are longitudinally stretched as the diaper 1 is put on the wearer's body. In the crotch region 21, the top wall sheet 11 narrower than the panel structure 2 inclusive of the second side flaps 12 are tightly placed against the wearer's inguinal region and the first side flaps 6 of the panel structure 2 are tightly placed against inner sides of the wearer's thighs. In the front and rear waist regions 20, 22, the first side flaps 6 of the panel structure 2 cover the wearer's belly and hip and the top wall sheet 11 inclusive of the second side flaps 12 cover the wearer s belly and hip over a large extent.

In the front and rear waist regions 20, 22, the end portions 11b of the respective side wall sheets 10 and the end portions 11b of the top wall sheet 11 are bonded to the panel structure 2, and the transversely opposite side edge portions 6a, 12a as well as the longitudinally end portions 6b, 12b of the first side flaps 6 and the second side flaps 12, respectively, are also bonded to the panel structure 2. In the front and rear waist regions 20, 22, therefore, movement of the sheet member 9 particularly in the transverse direction is restricted by the panel structure 2 and it is not apprehended that the sheet member 9 might move independently of the panel structure 2.

In the crotch region 21, only the side edge portions 10a of the respective side wall sheets 10 are bonded to the panel structure 2 and correspondingly the movement of the sheet member 9 is not so restricted by the panel structure 2 as in the front and rear waist regions 20, 22. In the crotch region 21 to which the wearer' movement is easily transmitted, the sheet member 9 does not follow the movement of the panel structure 2 even if the panel structure 2 follows the wearer's movement. Thus the top wall sheet 11 inclusive of the second side flaps 12 is maintained in close contact with the wearer's body.

In the diaper 1, the panel structure 2 may comprise the topsheet 3 and the backsheet 4 both being non-stretchable so far as at least the top wall sheet 11 constituting the sheet member 9 is elastically stretchable. In this case, the top wall sheet 11 may be bonded under longitudinal tension to the panel structure 2 in order to ensure that the side wall sheets 10 are biased to rise above the topsheet 3 and the top wall sheet 11 is biased to be spaced apart from the topsheet 3. It is also possible to form between the top edge portions 10c of the respective side wall sheets 10 with a pair of openings in the top wall sheet 11.

While the diaper 1 has been illustrated and described in which the first side flaps 6 and the second side flaps 12 are bonded together along the transversely opposite side edge portions 6a, 12a and the longitudinally opposite end portions 6b, 12b of these flaps 6, 12, it is also possible to bond these flaps 6, 12 along the transversely opposite side edge portions 6a, 12a thereof.

The topsheet 3 may be formed from a liquid-pervious sheet such as a nonwoven fabric or porous plastic film, preferably with a liquid-pervious hydrophilic sheet. The backsheet 4 and the sheet member 9 may be formed from a hydrophobic nonwoven fabric, liquid-impervious plastic film or a laminated sheet of a hydrophobic nonwoven fabric and a plastic film, preferably by a breathable but liquid-impervious sheet. It is also possible to form the backsheet 4 from a composite nonwoven fabric (SMS nonwoven fabric) consisting of a melt blown nonwoven fabric having a high water-resistance and two layers of spun bond nonwoven fabric having high strength and flexibility sandwiching the melt blown nonwoven fabric.

The nonwoven fabric may be selected from a group including spun lace-, needle punch-, melt blown-, thermal bond-, spun bond-, chemical bond- and air through-nonwoven fabric. Component fiber of the nonwoven fabric may be selected from a group including polyolefine-, polyester- and polyamide-based fibers and polyethylene/polypropylene or polyethylene/polyester core-sheath type conjugated fiber and side-by-side-type conjugated fiber.

The core 5 is a mixture of fluff pulp, high absorption polymer particles and thermoplastic synthetic resin fiber compressed to a desired thickness. The high absorption polymer may be selected from a group including starch-, cellulose-based polymer and synthetic polymer. Starch- and cellulose-based polymer may be graft polymer or carboxymethylated polymer. Synthetic polymer may be acryl-, POVAL-, acrylamide- or polyoxyethylene-based polymers.

Bonding of the top- and backsheets 3, 4, the sheet member 9 and the core 5 as well as attaching of the elastic member 8 may be carried out using suitable adhesive such as hot melt adhesive or heat-sealing technique.

In the disposable diaper according to this invention possible movement of the sheet member in the front and rear waist regions is well restricted by the panel structure. So far as the front and rear waist regions of the panel structure is properly put on the wearer's body, there is no anxiety that the sheet member might transversely shift independently of the panel structure and, in consequence, the opening also might shift.

In the crotch region, the movement of the sheet member is not so restricted by the panel structure as in the front and rear waist regions. Even if the panel structure moves in the crotch region to which the wearer' movement is easily transmitted, the sheet member does not follow the movement of the panel structure and the top wall sheet inclusive of the second side flaps is maintained in close contact with the wearer's body.

What is claimed is:

1. A disposable diaper comprising:
    a panel structure; and
    a sheet member,
    said panel structure including:
        a liquid-impervious base sheet;
        a liquid-absorbent core a attached to the liquid-impervious base sheet, said liquid-absorbent core having transversely opposite hide edges;
        a front waist region;
        a rear waist region;
        a crotch region extending between said front waist region and said rear waist region;
        a pair of first side flaps extending in a longitudinal direction immediately outside transversely opposite sides edges C said liquid-absorbent core;
        a pair of end flaps extending in a transverse direction immediately outside longitudinally opposed ends of said liquid-absorbent cut core, and
    said sheet member including:
        a pair of side walls extending in said longitudinal direction in the vicinity of the transversely opposite side edges of said liquid absorbent core so that said side walls are normally biased to rise above said panel structure;
        a top wall extending between top edges of said pair of side walls in parallel to said base sheet so that said top wall is normally biased to be spaced apart upward from said panel structure;
        said side walls respectively comprising side edge portions bonded to side flaps that extend outwardly of the transversely opposite side edges of the liquid-absorbent core and first end portions bonded to said end flaps, said top wall having at least one opening defined between said side walls and second end portions bonded to said end flaps a that a cavity configured to receive excretion is defined between said panel structure and said sheet member, said at least one opening having opposed transverse edges, said top wall having a pair of second side flaps extending immediately outside said top edges of said side walls in parallel to said first side flaps so that said first and second side flaps are bonded together at least along the transversely opposite side edge portions of said first and second side flaps overlapping each other in said front and rear waist regions, said top edges of said side walls being bonded to said top wall along the opposed transverse edges of the at least one opening and said side edge portions of said side walls being bonded to said side flaps so that said top wall is allowed to raise above the panel member with the side walls extending transversely inward from said side flaps to the transverse edges of the at least one opening.

2. The disposable diaper according to claim 1, wherein at least said top wall of said sheet member is elastically stretchable at least in said longitudinal direction of said longitudinal and transverse directions and bonded under tension in said longitudinal direction to said panel structure so that said side walls are normally biased to rise above said base sheet and said top wall is normally biased to be spaced apart from said base sheet.

3. The disposable diaper according to claim 1, wherein said first flap and said second side flap have transversely opposite side edges thereof curving inward in said transverse direction in said crotch region so as to describe circular arcs so that said top wall has a transverse dimension in said crotch region which is smaller than the corresponding dimension in said panel structure.

4. The disposable diaper according to claim 1, wherein transverse portions of the top wail extend transversely outward along the opposite transverse edges of the at least one opening and are allowed to raise above an apart from the side walls.

* * * * *